United States Patent
Youmans et al.

(10) Patent No.: US 6,615,409 B2
(45) Date of Patent: Sep. 9, 2003

(54) TINTED PLASTIC LENS FOR EYE PROTECTING DEVICES

(75) Inventors: Robert Youmans, Vashon, WA (US); David T. Robrahn, Ketchum, ID (US)

(73) Assignee: Scott USA, Inc., Sun Valley, ID (US)

( * ) Notice: Subject to any disclaimer, the term of this patent is extended or adjusted under 35 U.S.C. 154(b) by 0 days.

(21) Appl. No.: 10/014,082

(22) Filed: Dec. 11, 2001

(65) Prior Publication Data

US 2003/0110552 A1 Jun. 19, 2003

(51) Int. Cl.[7] .................................................. A61F 9/02
(52) U.S. Cl. ........................................................ 2/432
(58) Field of Search ........................... 2/426, 436, 443, 2/432, 441, 428, 439, 425; 351/44, 47, 159, 162, 163

(56) References Cited

U.S. PATENT DOCUMENTS

| | | | |
|---|---|---|---|
| 1,741,536 A | * 12/1929 | Rayton | 351/159 |
| 4,271,538 A | * 6/1981 | Montesi et al. | 2/439 |
| 4,826,286 A | * 5/1989 | Thornton, Jr. | 359/588 |
| 4,952,046 A | 8/1990 | Stephens | |
| 5,083,858 A | * 1/1992 | Girerd | 351/44 |
| 5,177,509 A | 1/1993 | Johansen | |
| 5,274,403 A | * 12/1993 | Gott | 351/47 |
| 5,400,175 A | 3/1995 | Johansen | |
| 5,408,278 A | 4/1995 | Christman | |
| 5,438,024 A | 8/1995 | Bolton | |
| 5,592,245 A | * 1/1997 | Moore et al. | 351/163 |
| 5,805,263 A | * 9/1998 | Reymondet et al. | 351/159 |
| 5,922,246 A | 7/1999 | Matsushita | |
| 5,926,310 A | 7/1999 | Tamura | |
| 5,975,695 A | 11/1999 | Baiocchi | |
| 5,997,139 A | 12/1999 | Yasuda | |
| 6,113,813 A | * 9/2000 | Goudjil | 252/586 |
| 6,119,276 A | * 9/2000 | Newcomb et al. | 2/425 |
| 6,138,285 A | * 10/2000 | Robrahn et al. | 2/436 |
| 6,138,286 A | 10/2000 | Robrahn | |
| 6,164,777 A | * 12/2000 | Li et al. | 351/162 |

OTHER PUBLICATIONS

"ChroMax B20, Un Nouveau Verre Pour Bausch & Lomb", L'Opto No. 55, May 1994, pp. 32–35.

* cited by examiner

Primary Examiner—Gary L. Welch
(74) Attorney, Agent, or Firm—Ronald L. Wanke; Jenner & Block, LLC

(57) ABSTRACT

A goggle has a replaceable plastic lens mounted in a flexible frame containing several air vents for passing external air through the goggle interior. The lens is formed of thermoplastic materials to provide spherical and cylindrical versions of the lens. The thermoplastic resins incorporate dyes which tint the lens to create a transmission curve with a broad flattened peak above a 50% transmission level and steep slopes to couple with the response characteristics of the rods of the human eye retina so as to improve contrast in very low light conditions such as night skiing under artificial light. Inlet and outlet air vents are covered by porous foam to reduce fogging in an outdoor environment.

26 Claims, 2 Drawing Sheets

//www.w3.org/1999/xhtml">
TINTED PLASTIC LENS FOR EYE PROTECTING DEVICES

TECHNICAL FIELD

This invention relates to a plastic lens which can be tinted to affect contrast and vision characteristics in low light conditions. It has applicability to eye protecting devices such as goggles used in an outdoor or other adverse environment, a safety goggle, eyeglasses, masks, and visors.

BACKGROUND OF THE INVENTION

Goggles which are intended for use in an outdoor or other adverse environment include sports goggles such as winter sports including skiing, snowboarding, snowmobiling, or motorcycle use, as well as safety goggles. Other eye protecting devices include eyeglasses, masks for helmets, and visors. Such eye protecting devices provide protection for the wearer's eyes from external air and particulate matter. A goggle for outdoor use may have vent apertures open to external air flow to exchange air between the exterior environment and the interior of the goggle. Such a vented exchange of air will minimize fogging caused by moisture in the air condensing on the lens of the goggle. The vent apertures are typically covered by a porous foam to control the air exchange while forming a partial barrier to snow, dust and other particulate matter. Such goggles can also include replaceable plastic lenses which may be a single lens or a double lens, and such lenses can be tinted in various colors to assist in contrast and glare protection.

Certain improved contrast resolution capabilities have been available in fixed glass lenses for eyeglasses and sunglasses, such as eyewear having a green or other colored lens which assists in contrast resolution capabilities. Goggles having a removable plastic lens which is tinted in a manner to improve contrast resolution for a wide variety of light levels including sunlight are disclosed in our U.S. Pat. No. 6,138,286 issued Oct. 31, 2000 and entitled "Goggle Having A Tinted Plastic Lens". The tint is adapted to the plastic materials usable in goggle lenses to provide improved visual performance and anti-fogging characteristics. In particular, the tint creates a transmission curve characterized by several peaks and valleys along the visible wavelength spectrum which conforms to certain characteristics of the human eye to improve contrast in a removable plastic lens useful in goggles for skiing and other outdoor sports.

While the eyewear described above provides improved contrast resolution capabilities for sunlight and certain low light conditions, there remains a need for improved performance in still lower light conditions including twilight and night use particularly when illuminated by artificial light sources. The types of known tinted lenses have less utility in very low light conditions such as night skiing on ski slopes which are artificially lighted.

SUMMARY OF THE PRESENT INVENTION

A tinted lens for goggles and other eyewear is provided which overcomes certain of the problems and disadvantages of prior tinted lenses and goggles using such lenses. Eye protecting devices utilizing the tinted lenses disclosed herein have particular utility in low light conditions such as, for example, determining changes in level of surfaces of a snow covered slope which is artificially lighted to allow night skiing.

In particular, the invention includes a tinted plastic lens of specialized characteristics having a transmission curve of particular shape and transmission levels which improve contrast in low light conditions, including night conditions which are artificially illuminated. The invention has particular utility for a winter sports goggle for night use on artificially lighted slopes or low light day use, but is also adaptable to eyewear for motorcycle use, safety shields, visors, safety goggles and the like which are to be used in low light conditions.

A better understanding of the present invention along with other objects and advantages will become apparent from the following description and with reference to the following drawings.

DESCRIPTION OF THE PREFERRED EMBODIMENTS

Figure 1:
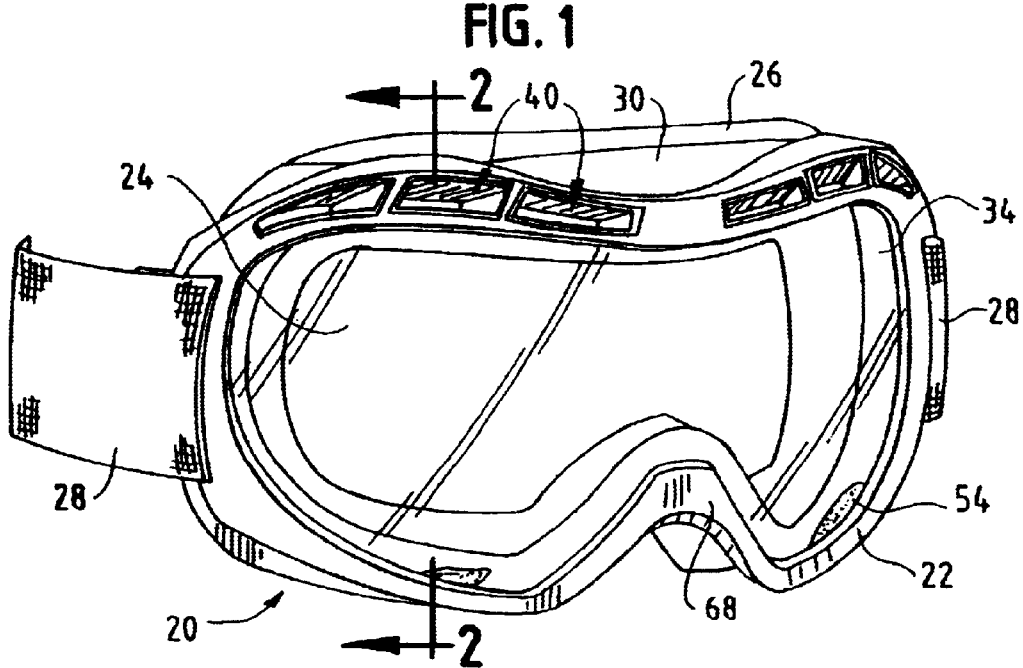
FIG. 1 is a perspective view of a novel plastic lens as used in a goggle.

As seen in the drawings, a goggle 20 which is particularly useful in an outdoor environment, although not limited thereto, includes a plastic flexible frame 22 which surrounds the eye region of a wearer. A front lens 24 of plastic material is removably mounted at the forward area of the surrounding frame 22 in order to protect the wearer's eyes. A flexible face padding 26 is glued or otherwise affixed to the rear of the frame 22 in order the cushion the frame against the face of the wearer and create a partial seal against the wearer's face. An elastic headband strap 28 attaches to both sides of the frame 22 to secure the goggle to the wearer's head or to the back of a helmet, as appropriate. Typically, the strap 28 will include a buckle adjustment (not illustrated) in order to vary the length of the strap 28 so as to secure the goggle relatively snugly against the face of the wearer.

The flexible frame 22 includes a top portion 30, a bottom portion 32, and side portions 34 which are injection molded as one piece from a thermoplastic resin such as polycarbonate which results in a molded pliable frame which is relatively stiff as is conventional in vented sports goggles. The frame surrounding portions in conjunction with the front lens 24 defines an interior space 36, see FIG. 2, when the goggle is placed against the wearer's face.

Figure 2:
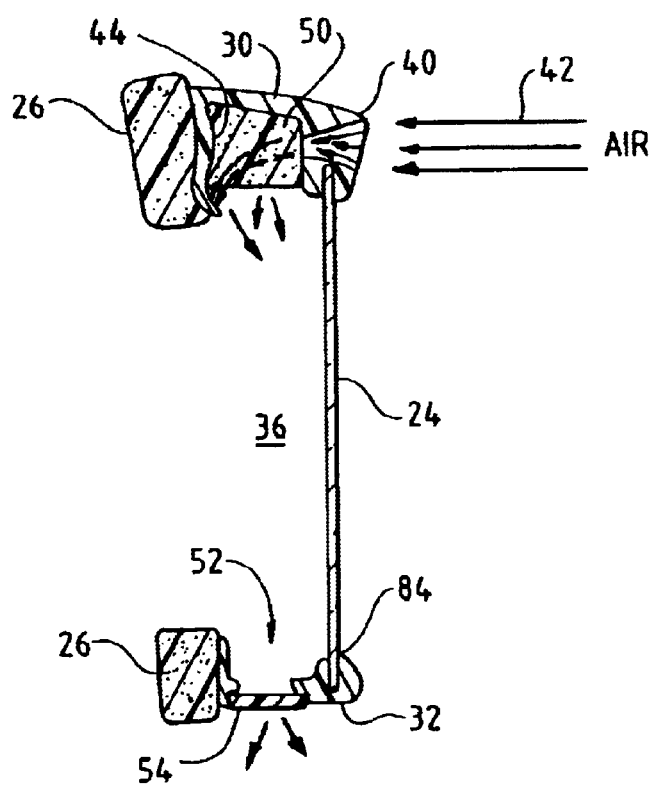
FIG. 2 is a side cross-sectional view of the goggle taken along lines 2—2 of FIG. 1.

As is seen best in FIGS. 1–2, the top portion 30 of the goggle frame is solid and has a generally smooth and planar extent, which can dip in the center. This smooth, solid, top surface forms a helmet contacting or mating surface for use when the goggle is worn in conjunction with a helmet. There are no vent apertures or other openings in the top portion 30. When a helmet is worn, the top planar surface will mate with and contact the helmet or helmet padding, in order to form a partial seal between the goggle top where it abuts the helmet. As a result, the goggle is particularly adapted for use with a helmet, although it is not limited to such use. The frame side portions 34 and/or bottom portion 32 have a variety of air vents located therein, for purposes of exiting air flow out of the goggle interior.

Along an elongated front upper section of the frame, beneath the top portion 30, a plurality of forward facing air scoops or air vents 40 are located to directly receive air as the wearer moves relatively in a forward direction. This frontal air, illustrated by the arrows 42 in FIG. 2, enters the forwardly facing air scoops 40 in large volumes compared to conventional goggles. The frontal air 42 is funneled through the inlet vent scoops 40 and into an upper chamber enclosed along its top and side and open downwardly to channel the frontal air into the goggle interior region 36. This upper chamber includes means for dispersing the air flow generally downward and with a forward component to improve interior venting of the goggle, but without rapid air flow across the wearer's eyes which could otherwise result if the forward-facing vents 40 directly communicated with the goggle interior.

The mechanism which redirects and disperses the forward air flow in a controlled manner includes the shape of the upper chamber 44 and, in addition, a permeable foam 50 located in the upper chamber 44. This foam 50 is of a porosity and size so as to redirect the air flow with reduced velocity and dispersement into the interior space 36 of the goggle.

In one embodiment, the foam 50 is a thick foam which may take all or substantial portion of the volume of the upper chamber. The dimensions of such foam can be approximately 16 mm by 16 mm by the longitudinal length of the upper chamber. The foam strip should be in intimate contact with the exit openings of the plurality of air scoops 40. It is formed of an open cell foam having a porosity of 20 to 80 pores per inch (ppi).

The air flow from the combination of the foam 50 and the upper air chamber moves in a generally downward direction through the interior space 36 and partly against the inside of the front lens 24. This air moves towards a plurality of exit vents 52 located in the frame bottom 32. The outlet vents 52 are formed as one or a plurality of apertures in the goggle frame. Preferably, the exit vents 52 are located in the bottom section 32 of the goggle frame so as to draw air from the top of the frame downwardly to exit at the bottom of the frame in the vicinity of the nose region. This serves to disperse moisture-laden air from the wearer's nose and thus assist in reducing fogging within the goggle. However, the exit apertures 52 also can be located in the side regions of the frame, in place of or in addition to the exit vents in the bottom section.

The exit vents 52 are covered with a thin permeable foam strip 54 which can be of 3 mm thickness and having an open cell porosity of 80 ppi. Preferably, the foam 50 associated with the inlet of air is different than the foam 52 associated with the exit of air to better control movement of air through the goggle interior.

A goggle of the type illustrated in FIGS. 1 and 2 is shown in more detail and various aspects are claimed in our U.S. Pat. No. 6,138,285, issued Oct. 31, 2000, entitled "Goggle For Sports and Adverse Environments," the contents of which are hereby incorporated by reference into this application.

Figure 3:
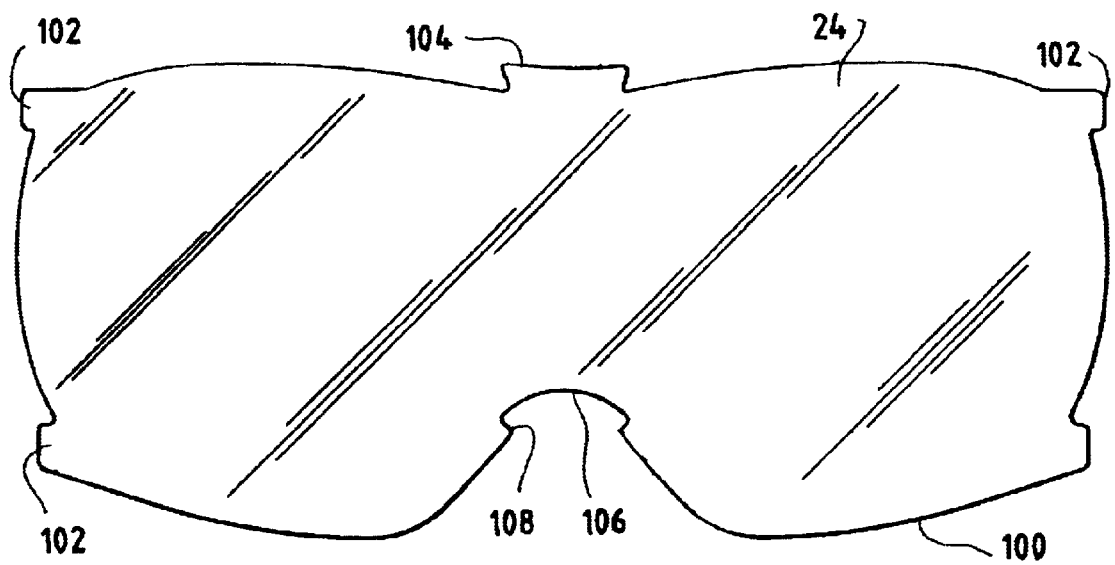
FIG. 3 is a front plan view of the removable plastic lens of the goggle of FIGS. 1 and 2.

As seen in FIGS. 2 and 3, the front lens 24 is formed of a plastic material and has a peripheral edge 100 of irregular shape which is inserted in a surrounding groove 84 of the frame for removable retention within the frame. The lens edge 100 includes projections for mating engagement with corresponding recesses in the peripheral groove 84. The lens projections include side ears 102 on each side of the lens 24, and a central upper tab 104. The lens 24 has a recessed nose area 106 which is received within a center nose bridge 68 of the goggle frame so that the interior space 36 surrounds the eyes of the wearer but does not encompass the wearer's nose. The recessed nose area 106 has projections 108 which serve as a notch to mate within recessed areas of the peripheral groove 84 to better retain the center portion of the lens within the goggle frame.

The lens 24 is replaceably mounted within the peripheral groove 84 by manipulating the flexible frame 22 so as to insert the peripheral edge 100 within the surrounding groove 84. When inserted, the various projections 102, 104, 108 extend into mating recesses within the peripheral groove 84 to assist in retaining the replaceable lens 24 within the goggle frame. In certain embodiments, the lens 24 is formed with a flexible shape, and the frame 22 is rigid or semi-rigid and forces the lens 24 into a curved shape when located in the mounting groove of the frame. In other embodiments, the lens 24 is injection molded into a curved shape, or is thermoformed into a curved shape by itself and/or is a thermal double lens with a spacer which is formed into a curved shape, all of which are self-supporting apart from mounting in the frame 22.

The plastic lens 24 is formed from a thermoplastic resin and may be formed as a spherical lens in order to have the best optical properties or as a cylindrical lens. Thermoplastic resins are linear polymers which can be melted and resolidified. Examples of suitable thermoplastic resins for the lens 24 are polycarbonate (PC) as well as the cellulosic family, as will be described.

In spherical lens embodiments, the plastic lens 24 is formed out of a polycarbonate (PC) material which is injection molded into a three-dimensional shape having an arcuate curve from top 104 to bottom 106 along its minor axis, and additionally an arcuate curve along its major axis from one side to the other side. In addition, the lens 24 can have a thickness which varies from the center region(s) to its edge 100. For example, in one embodiment, the lens has a maximum thickness of about 1.5 mm or less, such as 1.3 mm, which tapers to a thickness of 0.9 mm at the peripheral edge 100. The radii of curvature from top to bottom and side to side create an overall spherical shape with a varying thickness. Such a spherical lens is of very low weight and has good optical properties because it does not create any magnification or distortion. The resulting hard plastic lens will maintain its curved shape and has better optical qualities and impact resistance than a cylindrical plastic lens, albeit at an increased cost of production.

In other embodiments, the replaceable plastic lens 24 can be formed of several cellulosic thermoplastic resins based on cellulose, a complex carbohydrate chemically modified to produce a plastic. This cellulosic material is extruded flat with a constant thickness and press polished if desired. Then, the lens is stamped out of the flat sheet so as to have the shape illustrated in FIG. 3. The use of a cellulosic material produces a lens of low cost and reasonable quality. However, it is possible to use a polycarbonate material which is extruded flat or thermoformed. The resulting lens can be flat of constant thickness and flexible, or thermoformed into a self-supporting curved shape. When inserted into the peripheral groove 84, such a lens will curve from side to side following the curved shape of the frame 22, and hence is referred to as a cylindrical lens. Such a cylindrical plastic lens can be produced at relatively low cost and is satisfactory for many applications, although it does not have the superior optical qualities nor impact resistance of a hard lens of polycarbonate which is injection molded in spherical form as previously described. The cellulosic lens also can be thermoformed into a self-supporting curved shape.

The replaceable plastic lens 24, whether produced in the spherical embodiment or in the cylindrical embodiment, is desirably tinted or colored by pigment dyes incorporated into the thermoplastic resin to produce transparent colors to create a high contrast resolution lens as will be described. The composition of the dyes will vary depending on the composition of the plastic lens 24.

The human eye contains photoreceptors which are located in the retina. There are two types of photoreceptors, rods which primarily determine night vision and cones which provide high acuity (definition) and color vision in daytime light conditions. There are three types of cones in the retina of the human eye, each having a different pigment and different absorption curves. One set of cones is particularly receptive to blue light in the vicinity of about 400 to 450 nm, another set of cones is receptive to the absorption of green light around 525 to 575 nm, and the third set of cones is particularly susceptible to red or orange-red light in the vicinity of 550 to 600 nm. There is substantial overlap of these absorption curves and a broad range of wavelengths are absorbed to some extent by the pigments of all photoreceptors. Both rods and cones function to some degree at all times.

The responses of rods and cones both contribute to vision at intermediate and other low-level intensities of illumination. Furthermore, the human eye response is not directly related to the peaks of wavelengths per se, but rather to an integration of the spectral curve and relative ratios of intensities of the pigments of the cones and rods. At times only two cones are essentially effective. As light intensity falls, the human eye becomes increasingly sensitive to light of shorter wavelengths. At low light conditions such as twilight the eye is most sensitive to a blue-green light such as 510 nm.

In our U.S. Pat. No. 6,138,286 issued Oct. 31, 2000, entitled "Goggle Having A Tinted Plastic Lens", a tinted plastic lens having a high contrast tint had a transmission curve with an undulating or wavy shape with several peaks to approximate the sensitivity of the human eye to light of various wavelengths. The high contrast tint disclosed therein had two or three peaks of wavelengths which produced good coupling to the blue, green and red cone receptors of the human eye. The resulting tinted lens provided improved contrast in sunlight and certain low light conditions. However, this tint is less effective for very low light conditions such as night skiing on an artificially lit snow slope. The present invention is designed to provide improved contrast in these lower light conditions.

In general, the combination of pigments to be used to tint the lens 24 will vary depending on the thermoplastic resin used for the lens 24. Various dyes should be combined so as to approximate to a reasonable extent and at a reasonable cost the spectral curve discussed later with respect to FIG. 4. More particularly, the plastic lens 24 is desirably formed of a transparent thermoplastic resin which incorporates dye material so as to tint the lens to pass selected wavelengths and diminish other wavelengths, so as to create a response curve better correlated to the rod photoreceptors of the eye in very low light conditions. Due to the low level of light, the overall light transmission should be higher at the low ranges than would be acceptable for a lens for bright light daytime use. The lens can be formed as a single lens having the desired average light transmission characteristics to be described, or formed as a double lens in which one lens may have the desired light transmission characteristics and the other lens can be clear if desired, so long as the resulting transmissions are of the characteristics described herein. The lens should have a high optical quality and a high impact resistance. It should resist fogging. It should be comfortable under prolonged use and be durable.

Figure 4:
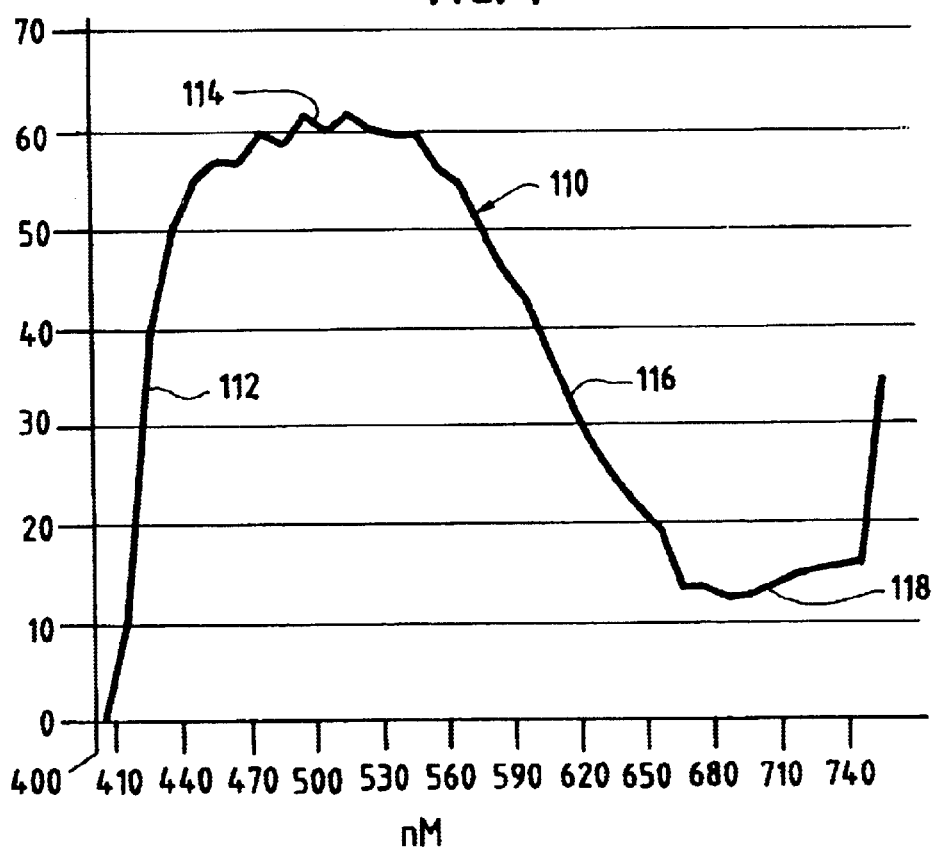
FIG. 4 is a transmission curve or spectral curve for the plastic goggle lens and showing light transmission versus wavelength.

In FIG. 4, a transmission curve 110 or spectral curve is illustrated for the tinted thermoplastic lens 24 of the present invention. For this transmission curve, the percentage (%) of light transmission through the lens is given for various visible wavelengths of light in nanometers or "nm," extending from 400 nm to about 700 nm. The transmission curve 110 comprises a single flattened peak of greater than 50% transmission in a range from about 430 nm to 570 nm, with very steep slopes leading to and from the flattened peak, and very low transmittance of generally less than 20% for the other visible wavelengths of light. This generally corresponds to and couples closely with the transmission curve of the rods of the human eye retina. The pigments described later should be selected to color match this desired transmission curve as closely as possible.

The transmission curve 110 includes a steep leading edge slope 112 which extends from almost 0% transmission to over 50% transmission from about 410 nm to about 430 nm and thus spans in a narrow range of about 30 nm. This steep rising slope 112 leads into a generally flattened broad peak or dome 114 above 50% transmission from about 430 nm to about 570 nm for a range of at least 100 nm and preferably about 140 nm. Although certain sharp angles are shown for the measurement points as listed in the following Table 1, this is not to scale, and the pigments will create continuous curves of smoother segments. The curved upper peak section 114 has a peak transmission of around 60%. This broad dome shape 114 then leads into a steep falling edge slope 116 which falls from a 50% transmission level at about 570 nm to about a 20% transmission level at about 650 nm for a range of less than 100 nm and preferably about 80 nm. The falling slope 116 is less steep than the rising slope 112 but still has a substantial rate of change of transmission levels. The falling slope 116 then leads into a generally flattened valley 118 of less than 20% transmission for generally the remaining range of visible light from about 650 nm to at least 740 nm, for a range of about 90 nm. The wavelength range of the falling slope 116 is approximately co-extensive with the wavelength range of the valley 118. The average transmission over the entire spectrum from about 400 nm to about 700 nm is desirably greater than 30% and preferably is approximately 34%. However, this average transmission is unbalanced across the visible wavelength range and is very substantially higher in the lower range from about 430 nm to about 650 nm.

Compared with a glass lens with a tinted green color, for example, the transmission curve 110 is much steeper on both rising and falling side slopes 112 and 116, and has a flatter broad top 114 as well as a flatter lower transmission valley 118 before rising again. These particular characteristics will couple closely with the rods of the human eye, and therefore enhance contrast and vision in very low light conditions. It should be noted that the tint 110 is designed to improve contrast in low level light conditions where shadow and shades of grey are important, and the tint 110 is not designed to transmit accurately the colors of external objects.

The transmission curve 110 for a tinted polycarbonate lens can be produced by incorporating dopants or pigments into the polycarbonate resin prior to injection molding. The quantity of pigments needed depends on the average filtration level that is required, the concentration of the pigments, and the thickness of the lens. The quantities of pigment added into the polycarbonate material are measured in parts per million or ppm. According to the different thickness of the lens in association with the filtration levels, the quantities may vary from less than 10 ppm to more than 200 ppm. Variations in the pigment levels and tolerances will have an influence on the transmission level.

More particularly, the following Table 1 lists the percent (%) transmission of light for wavelengths in nm for the polycarbonate lens 24 using the tint 110 of FIG. 4.

TABLE 1

| Wavelength | Transmission |
|---|---|
| 400 | 0.0% |
| 410 | 9.5% |
| 420 | 38.9% |
| 430 | 49.9% |
| 440 | 54.9% |
| 450 | 56.9% |
| 460 | 56.7% |
| 470 | 59.6% |
| 480 | 58.5% |
| 490 | 61.5% |
| 500 | 59.8% |
| 510 | 61.5% |
| 520 | 60.0% |
| 530 | 59.5% |
| 540 | 59.5% |
| 550 | 56.0% |
| 560 | 54.3% |
| 570 | 49.8% |
| 580 | 45.8% |
| 590 | 42.7% |
| 600 | 37.4% |
| 610 | 32.2% |
| 620 | 27.9% |
| 630 | 24.3% |
| 640 | 21.7% |
| 650 | 19.4% |
| 660 | 13.3% |
| 670 | 13.3% |
| 680 | 12.1% |
| 690 | 12.4% |

While the above Table 1 and transmission curve 110 of FIG. 4 illustrate one preferred embodiment for the tinted lens 24, it should be understood that the transmission curve can be varied somewhat.

In a spherical lens embodiment, the plastic lens 24 is desirably formed from a polycarbonate (PC) material which can be injection molded to create a hard lens blank having a varying thickness. To create an overall spherical geometry or shape, the lens blank may have multiple radii to reduce distortion. Examples of spherical lens shapes and a process of manufacturing lens blanks are illustrated in U.S. Pat. No. 1,741,536 to Rayton entitled "Goggles," issued Dec. 31, 1929, U.S. Pat. No. 4,271,538 to Montesi et al., entitled "Safety Spectacles," issued Jun. 9, 1981, and U.S. Pat. No. 5,805,263 to Reymondet et al., entitled "Lens Blanks, Process Of Manufacture Therefor And Eyewear Incorporating Lenses Made Therefrom," issued Sep. 8, 1998. The blank may be stamped or cut with a peripheral edge shape as illustrated in FIG. 3 by a lens manufacturer in order to produce a replaceable lens member usable with a goggle. Alternatively, the lens blank can be supplied to a goggle manufacturer who can then die cut the lens blank into the appropriate shape to form the replaceable lens member for the goggle. The resulting PC lens member will have a high impact resistance as is desirable for sports goggles and safety goggles. The PC lens may be treated with a coating in order to improve scratch resistance.

In a cylindrical lens embodiment, the plastic lens 24 is preferably made out of the cellulose family. In particular, the lens can be formed from cellulose acetate (CA), cellulose acetobutyrate (CAB), or cellulose acetopropionate (CAP). Typically, these cellulosics are compounded with plasticizers and are then extruded into a flat sheet of constant thickness. The optical quality of the flat sheet can be improved by placing the cellulosic sheet between chemically polished metal sheets and then pressing the laminate at high pressure and temperature, in a process known as press polishing. This improves the optical clarity of the sheet and reduces surface defects that will impair vision. The resulting cellulosic lens member can then be cut or stamped so as to have the peripheral edge shape of FIG. 3 in order to form a replaceable lens for a goggle. It can be thermoformed into a self-supporting curved shape, and/or combined with another lens and a spacer to form a thermal double lens useful for winter sports.

The goggle lens 24 when made from cellulosics material such as CAB, CAP, or CA, has a lower impact resistance than the spherical lens made of polycarbonate but with a sufficient impact resistance to be used in a goggle. The impact resistance will vary with the amount of plasticizer added for processing. In general, the lens 24 when formed of CAP will have the highest impact resistance for a cellulosics lens, with CAP being a close second, and CA being considerably below CAP.

For use in an outdoor or adverse environment, it is desirable that the plastic lens 24 should resist fogging caused by an increase in relative humidity in the interior space 36. The venting of the goggle interior through the inlet vents 40 and outlet vents 52 assists to reduce the relative humidity. In addition, the lens 24 can be surface treated with an anti-fogging coating to cause water on the interior side of the lens to bead or form a film.

In particular, the plastic lens 24 when formed of cellulosic material is desirably treated by immersion into a solution that chemically treats both surfaces or at least the inner surface adjacent interior space 36. This treatment is done in sheet form prior to forming. The result is a surface that initially absorbs moisture until saturation, and then causes additional moisture to form as a film of water rather than beads. When the plastic lens 24 is formed of a polycarbonate material, an anti-fogging coating can be applied to one or both surfaces by dipping the lens into a solution. The result is a surface which tends to form beads of water on the treated side of the lens.

When the goggle is to be used in cold temperatures, the lens 24 can be of double lens construction, often referred to as a thermal lens. The outer lens can be a thin, injection molded, spherical lens of polycarbonate material which is hard-coated on both sides. The polycarbonate material is colored with the tint described previously. The inner lens can be formed of clear cellulosic material such as CAP having for example a 0.020 to 0.036 inch thickness with an anti-fog treatment on one or both sides. To ensure preciseness in curvature, it should be thermoformed to match the inner radius of the outer PC lens. The inner and outer lens can be separated by a gasket spacer, as for example a 0.125 inch thick foam with adhesive on both sides around the entire peripheral edge. The pair of lens can be attached to the gasket to maintain a self-supporting curved shape.

Further modifications and changes to the invention can be made without departing from the scope of the invention.

What is claimed is:

1. An eye protecting device for low light conditions comprising:
   a frame having sections surrounding a wearer's face including a frame mounting portion, a plastic lens formed of a thermoplastic resin and mountable in the frame mounting portion in spaced relation in front of the wearer's face, the thermoplastic resin incorporating dye material to tint the plastic lens to transmit variable amounts of light over a range of wavelengths between 400 nm and 700 nm, the tinted plastic lens having a transmission curve with a steep rising slope extending to a flattened top having a range of at least 100 nm and over 50% transmission, the flattened to extending to a steep falling slope of less than 100 nm followed by a flattened valley of less than 20% transmission to thereby improve contrast for a wearer in low light conditions.

2. The device of claim 1 wherein the thermoplastic resin is comprised of polycarbonate material which forms the plastic lens.

3. The device of claim 1 wherein the thermoplastic resin is comprised of cellulosic material which is extruded into a sheet which forms the plastic lens.

4. The device of claim 3 wherein the cellulosic material is extruded into a flat sheet of constant thickness, the frame mounting portion having a curved shape, and the plastic lens being mountable therein to create a cylindrical lens of constant thickness.

5. The device of claim 1 wherein the thermoplastic resin is selected from one of a class of polycarbonate material and cellulosic material and thermoformed into a curved lens which maintains a curved shape before being mounted in the frame mounting portion.

6. The device of claim 1 wherein said flattened to of over 50% transmission has a broad dome shaped curve located in the vicinity of rod photoreceptors in a human eye retina.

7. The device of claim 1 wherein said flattened to has over 50% transmission and less than 70% transmission and is located in the vicinity of about 430 nm to about 570 nm.

8. The device of claim 7 wherein the steep falling slope extends from about 570 nm to less than 670 nm.

9. The device of claim 7 wherein the flattened valley of less than 20% transmission has a greater than 10% transmission and extends from about 650 nm to more than 700 nm and then has a rising slope above 20% transmission.

10. The device of claim 1 wherein the plastic lens has an average transmission of light in a range of above 30%.

11. A goggle for low light conditions comprising:

a replaceable plastic lens formed of a thermoplastic resin and containing mounting projections, a frame having sections surrounding a wearer's face including a lens mounting portion for mating engagement with the mounting projections to replaceably mount the lens in spaced relation in front of the wearer's face to define an interior space, the plastic lens having a tint producing a transmission curve for visible light with an average transmission through the lens above 30% and a flattened top of greater than 50% transmission for a range of wavelengths between 400 nm and about 570 nm to create a dome shape, the flattened top being followed by a steep falling slope which falls to a flattened valley below 20% transmission for wavelengths above the steep falling slope.

12. The goggle of claim 11 wherein the flattened top of greater than 50% transmission corresponds to absorption bands of rods in a human eye retina so as to improve contrast resolution for low visible levels of light passing through the plastic lens.

13. The goggle of claim 11 wherein the flattened top forms a broad curve creating the dome shape from about 430 nm to about 570 nm.

14. The goggle of claim 11 wherein the steep falling slope extends between about 570 nm to about 650 nm and the flattened valley then is followed by a rising slope above 20% transmission.

15. The goggle of claim 11 including vent means located in the frame sections to vent external air pass an inner surface of the plastic lens, and the plastic lens is treated with an anti-fogging coating to further reduce fogging on the plastic lens.

16. The goggle of claim 11 wherein the plastic lens is formed of polycarbonate material which is formed in a spherical shape to create a spherical lens.

17. The goggle of claim 11 wherein the plastic lens is formed of cellulostic material which is extruded into a sheet of constant thickness to create a flexible cylindrical lens of constant thickness which curves when the mounting projections are in mating engagement with the lens mounting portion of the frame.

18. The goggle of claim 11 wherein the plastic lens is selected from one of a class of polycarbonate material and cellulosic material and is thermoformed into a curved replaceable plastic lens which maintains a curved shape before being replaceably mounted in the lens mounting portion.

19. A plastic lens member for low light conditions, wherein the lens member is formed of a thermoplastic resin which incorporates dye material to tint the lens to produce a transmission curve for visible light over a range of wavelengths between 400 nm and 700 nm, the transmission curve having a dome shape of greater than a 50% transmission for a first range of wavelengths between 400 nm and about 570 nm followed by a steep falling slope for a second range of wavelengths of less than 100 nm followed by a flattened valley of less than 20% transmission to improve contrast for low levels of visible light passing through the lens member.

20. The plastic lens member of claim 19 wherein the tint produces an average transmission through the lens member of above 30%.

21. The plastic lens member of claim 19 wherein the thermoplastic resin is comprised of a polycarbonate material which forms the lens member.

22. The plastic lens member of claim 19 wherein the thermoplastic resin is comprised of a cellulosic material which is extruded into a sheet of fixed thickness to form the lens member.

23. The plastic lens member of claim 19 wherein the dome shape is created by a flattened curved shape related to absorption bands of rods in a human eye retina so as to improve contrast resolution for low levels of visible light passing through the lens member.

24. The plastic lens member of claim 19 wherein the lens member has an irregular peripheral shape with mounting projections forming a tinted plastic lens for attachment by at least the mounting projections to a goggle frame.

25. The plastic lens member of claim 19 wherein the thermoplastic resin includes one of a class of polycarbonate and cellulosic material, and the lens member is thermoformed into a self-supporting curved shape.

26. The plastic lens member of claim 19 wherein the lens member is a lens blank for the manufacture of a tinted plastic lens.

* * * * *